United States Patent [19]
Sheen et al.

[11] Patent Number: 5,859,609
[45] Date of Patent: Jan. 12, 1999

[54] REAL-TIME WIDEBAND CYLINDRICAL HOLOGRAPHIC SURVEILLANCE SYSTEM

[75] Inventors: David M. Sheen; Douglas L. McMakin, both of Richland; Thomas E. Hall, Kennewick; Ronald H. Severtsen, Richland, all of Wash.

[73] Assignee: Battelle Memorial Institute, Richland, Wash.

[21] Appl. No.: 714,026

[22] Filed: Sep. 11, 1996

Related U.S. Application Data

[63] Continuation-in-part of Ser. No. 440,279, May 12, 1995, Pat. No. 5,557,283, which is a continuation-in-part of Ser. No. 212,432, Mar. 14, 1994, Pat. No. 5,455,590, which is a continuation-in-part of Ser. No. 963,204, Nov. 23, 1992, abandoned, which is a continuation-in-part of Ser. No. 752,750, Aug. 30, 1991, abandoned.

[51] Int. Cl.$^6$ .............................. G01S 13/89; G03H 5/00
[52] U.S. Cl. ................................................ 342/179; 367/8
[58] Field of Search ................................. 342/179; 367/8; 364/827

[56] References Cited

U.S. PATENT DOCUMENTS

| | | | |
|---|---|---|---|
| 5,073,782 | 12/1991 | Hugenin et al. | 342/179 |
| 5,170,170 | 12/1992 | Soumekh | 342/179 |
| 5,455,590 | 10/1995 | Collins et al. | 342/179 |
| 5,557,283 | 9/1996 | Sheen et al. | 342/179 |

OTHER PUBLICATIONS

K. Sigfrid Yngvesson, et al., "Endfire tapered Slot Antennas on Dielectric Substrates," IEEE Transactions on Antennas and Propagation, vol. AP–33, No. 12, Dec. 1985, pp. 1392–2000.
G. Tricoles, et al., "Microwave Holography: Applications and Techniques," Proceedings of the IEEE, vol. 65, No. 1, Jan. 1977, pp. 108–121.
N. H. Farhat, "High Resolution Micro3wave Holography and the Imaging of Remote Moving Objects," Optical Engineering, Sep.–Oct. 1975, vol. 14, No. 5, pp. 499–505.
G.F. Abbott, "Personal Surveillance System" IBM Technical Disclosure Bulletin, vol. 12, No. 7, Dec. 1969, pp. 1119–1120.
M. Soumekh, Fournier Array Imaging, Published by PTR Prentice Hall, Englewood Cliffs, NJ, 1994, pp. 339–348.

*Primary Examiner*—Ian J. Lobo
*Attorney, Agent, or Firm*—Paul W. Zimmerman

[57] ABSTRACT

A wideband holographic cylindrical surveillance system including a transceiver for generating a plurality of electromagnetic waves; antenna for transmitting the electromagnetic waves toward a target at a plurality of predetermined positions in space; the transceiver also receiving and converting electromagnetic waves reflected from the target to electrical signals at a plurality of predetermined positions in space; a computer for processing the electrical signals to obtain signals corresponding to a holographic reconstruction of the target; and a display for displaying the processed information to determine nature of the target. The computer has instructions to apply Fast Fourier Transforms and obtain a three dimensional cylindrical image.

9 Claims, 7 Drawing Sheets

ARRAY ROTATES AROUND PASSENGER

REAL-TIME WIDEBAND CYLINDRICAL HOLOGRAPHIC SURVEILLANCE SYSTEM

This application is a Continuation-In-Part of U.S. patent application Ser. No. 08/440,279 filed May 12, 1995, now U.S. Pat. No. 5,557,283, which is a Continuation-In-Part of U.S. patent application Ser. No. 08/212,432, filed Mar. 14, 1994, now U.S. Pat. No. 5,455,590 issued Oct. 3, 1995, which is a Continuation-In-Part of U.S. patent application Ser. No. 07/963,204, filed Nov. 23, 1992, now abandoned, which is a Continuation-In-Part of U.S. patent application Ser. No. 07/752,750, filed Aug. 30, 1991, now abandoned.

STATEMENT OF GOVERNMENT INTEREST

This invention was made with Government support under Contract DE-AC06-76RLO 1830, awarded by the U.S. Department of Energy. The Government has certain rights in the invention.

FIELD OF THE INVENTION

The present invention relates to a method and apparatus useful for inspection of concealed objects. More specifically, the present invention relates to forming a cylindrical image with millimeter wave signals that are transmitted and received by a holographic array and that are reconstructed using Fast Fourier Transform Analysis. The method and apparatus have particular utility for personnel inspection in mass transportation centers.

BACKGROUND

The need for a new and more versatile personnel inspection system in mass transportation centers has increased in recent years. Extensive description of traditional and holographic methods is provided in U.S. Pat. No. 5,455,590, hereby incorporated by reference.

The holographic linear array of sequentially-switched millimeter-wave transmitter-receivers scanned quickly over a large aperture to actively illuminate the target as described in U.S. Pat. No. 5,455,590 uses a single frequency that is coherent, which means the phase of the returned signal is recorded as well as the amplitude. The holographic linear array described in U.S. patent application Ser. No. 08/440, 279 improves image quality by using a wideband system.

U.S. Pat. No. 5,170,170 to Soumekh show a two-dimensional reconstruction process. In his book entitled FOURIER ARRAY IMAGING, Englwood Cliffs, N.J., Prentice Hall, 1994, Soumekh derived a reconstruction process for a circular aperture resulting in a two-dimensional image.

However, the previous systems lack the capability of scanning an individual from all sides quickly without inconveniencing the individual. Specifically, to fully inspect a person for concealed objects, it is necessary to image the person from many viewing angles. With a planar aperture, a person is required to pose at a number of predetermined positions while images are acquired. To obtain a sufficient number of images (8-128), total imaging time may be as high as several minutes, which is unacceptable for high throughput applications including airports.

Thus, there is a need for a three-dimensional holographic imaging method and apparatus that can provide high resolution with fast scanning and fast image reconstruction.

SUMMARY OF THE INVENTION

The present invention disclosed herein involves a method and apparatus for achieving near real-time holographic imaging of concealed objects. A vertical linear antenna array is actuated over a circular path to obtain a 360° cylindrical scan of a covered target, for example a clothed individual. The data are in the form of unfocused or diverging millimeter wave illumination which is capable of penetrating a cover, for example clothing. The millimeter wave illumination must be mathematically focused or reconstructed into recognizable images. A completely new reconstruction algorithm is required to accept the wideband data gathered over a section of the 360° cylindrical aperture and form a fully focused three-dimensional image. Subsets of the 360° data may be used to form images of the target from any cylindrical viewing position or viewing angle. Complete inspection of the target is accomplished by a single scan of the vertical linear antenna array about the circumference of the cylinder in several seconds. Computer generated animation permits sequential viewing of images incremented by viewing angle. When the increments are small enough, the image will appear that the target is rotating slowly. An operator is then able to fully visually inspect the target for concealed objects.

The present invention is an extension of the holographic imaging system from planar imaging operation viewing a single side to cylindrical imaging operation viewing multiple sides. Rather than forming an image of one side, for example a front view, the invention forms images from multiple sides. Wideband data are gathered over a two-dimensional cylindrical aperture. The use of a cylindrical aperture overcomes the single viewing angle limitation present in a planar aperture system. In this specification, the term wideband refers to integrated sending and receiving of at least two frequencies, as opposed to separate sending and receiving of at least two frequencies.

The wideband or broadband parameters with respect to number of frequencies, and range of frequencies are described in the U.S. Pat. No. 5,557,283 hereby incorporated by reference. Moreover, U.S. Pat. No. 5,557,283 describes the antenna array and bi-static, heterodyne, in- phase transceiver preferred for cylindrical imaging, as well as alternative transceivers useful for cylindrical imaging.

In this patent application, the cylindrical scanner and the reconstruction algorithms are described.

It is an object of the present invention to provide a cylindrical wideband millimeter-wave imaging method and apparatus.

It is a further object of the present invention that the method and apparatus have an expanded depth of field and providing views or images from multiple viewing angles or multiple sides to accomplish near real-time imaging that is needed for personnel surveillance.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION OF THE INVENTION

The following description begins with a description of a wideband cylindrical holographic imaging system followed by a derivation of a wideband cylindrical reconstruction algorithm. Operational Examples are then provided.

WIDEBAND CYLINDRICAL HOLOGRAPHIC SYSTEM

Figure 1:
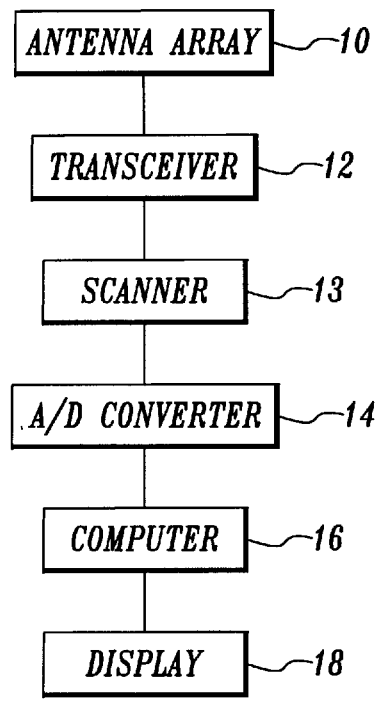
FIG. 1 is a block diagram of a cylindrical wideband holographic system.
Figure 2:
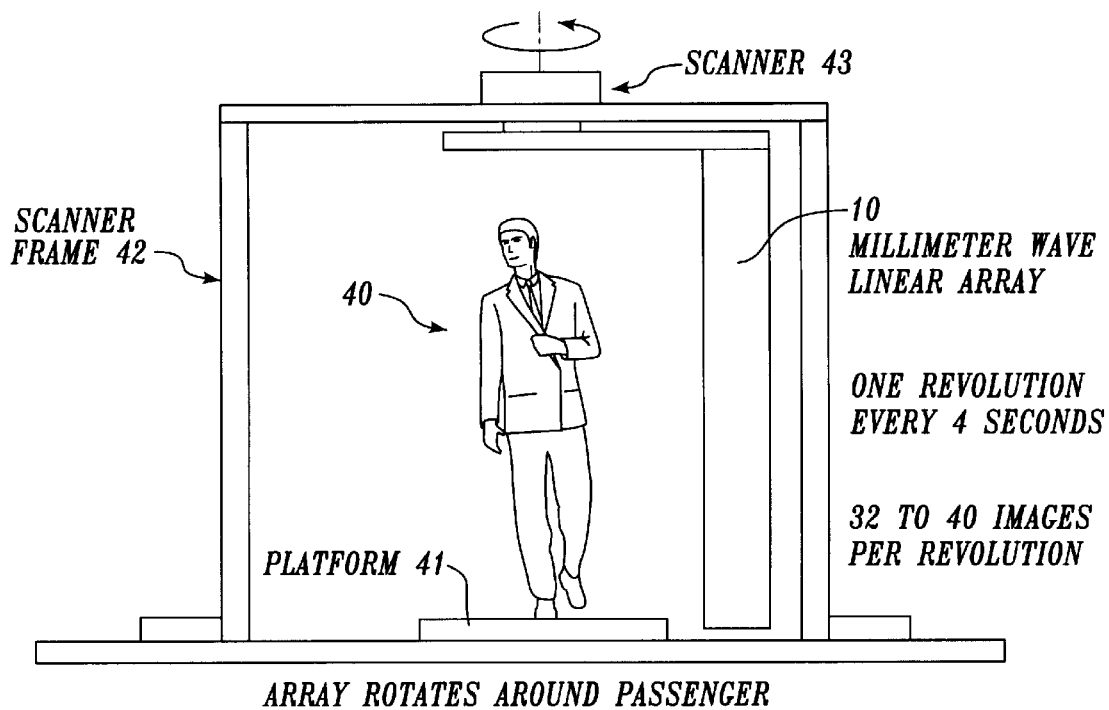
FIG. 2 is a conceptual diagram of a cylindrical wideband holographic system.

The wideband cylindrical holographic system (FIG. 1) is made up of an antenna array 10, transceiver 12, scanner 13, A/D converter 14, computer 16, and display 18. A system diagram (FIG. 2) shows a person 40 on a platform 41 within a scanner frame 42. The antenna array 10 is rotated about the person 40 to obtain the image(s).

The person 40 to be scanned is directed to stand relatively still on the platform 41 of the scanner frame 42 while vertical linear antenna array 10 around the person 40 in a cylindrical manner. Millimeter-wave illumination from the antenna array 10 passes through clothing and is reflected from concealed objects. The reflected millimeter-wave signals are recorded by the imaging system and focused, or reconstructed, using a computer 16 into recognizable images of the subject revealing concealed objects.

CYLINDRICAL SCANNER

The cylindrical scanner's 43 function is simply to rotate the vertical antenna array(s) 10 about the target being scanned. For a person as a target, this requires a scanner approximately 2 meters in height. The radius of the scan should be in the range of 0.75 meters–1.25 meters. The radius must be large enough that a person can easily enter and exit the system and should be as small as possible to minimize the footprint, or floorspace, required of the scanner.

LINEAR ANTENNA ARRAY

The antenna array 10 spans the vertical length of the aperture, typically about 2 meters for personnel surveillance. The millimeter-wave source is switched to each antenna element in the array. The array can be configured to transmit and receive from the same antenna element, however, a preferred configuration uses separate transmit and receive arrays. Logic circuitry sequences the transmit and receive antennas to transmit from one antenna and receive the reflected wideband signal from each of the two neighboring antennas in the receive row. This places a virtual sampling point half-way between each transmit and receive antenna. The transmit row and receive row are preferably offset by half the antenna spacing, so the effective sample spacing is one-half of the single-row antenna spacing. This sequencing scheme cannot be used on the last antenna element, so the effective number of sample points is reduced by one. The sampling density needed for the arrays is determined by the millimeter-wave center-frequency and by the Nyquist sampling criterion. Generally, sampling on the order of one-half wavelength is optimal, with two-thirds wavelength providing acceptable results. For a 2 meter vertical array operating at 27–33 GHz, this would indicate that 300–400 antenna elements will be needed.

For a wideband system, the antenna array 10 may be a single transmit/receive antenna element that is moved across a two-dimensional aperture. It is preferred, that the antenna 10 be an array of antenna elements that is at least a single row of a plurality of antenna elements. Alternatively, antenna elements may be arranged so that one row is a set of transmit antenna elements and a second row is a set of receive antenna elements. Separate transmit and receive antenna elements are preferred for a wideband system to avoid the need of a multi-frequency circulator.

TRANSCEIVER SWITCHES

Millimeter-wave switching is required in the cylindrical wideband holographic imaging system in order to provide high-speed sampling of the cylindrical aperture. Under high-speed electronic control, a single transmit antenna and a single receive antenna must be individually connected to the transceiver. It is possible to construct an array using commercially available single pole double throw (SPDT) pin-diode millimeter-wave waveguide switches, however, this array would be very bulky, and it would be difficult to arrange the outputs to have the desired spacing. To overcome this difficulty, a custom switch module, such as the single-pole 8-throw (SP8T) switch described in 08/440,279 hereby incorporated by reference, is desirable. Internally, the SP8T switch module uses a binary tree structure composed of three layers of SPDT switch elements for a total of 7 SPDT elements. Each SPDT element contains a duroid fin-line printed circuit junction which uses shunt pin-diodes to direct the millimeter-wave signal to the desired output waveguide. The pin-diodes are controlled by electronic driver circuitry mounted in a housing on top of a split-block (not shown). One of these SP8T modules may be connected to 8 other SP8T modules to form a 64 element switch sub-array. Several of these switch sub-arrays can then be connected to the vertical linear antenna array 10 with the required number of antenna elements.

ANTENNA ELEMENTS

The type of antenna element may be any type including but not limited to slot line, patch, endfire, waveguide, dipole, or any combination thereof. A preferred antenna element is a polyrod antenna element as described in 08/440,279 hereby further incorporated by reference.

TRANSCEIVER

Figure 3:
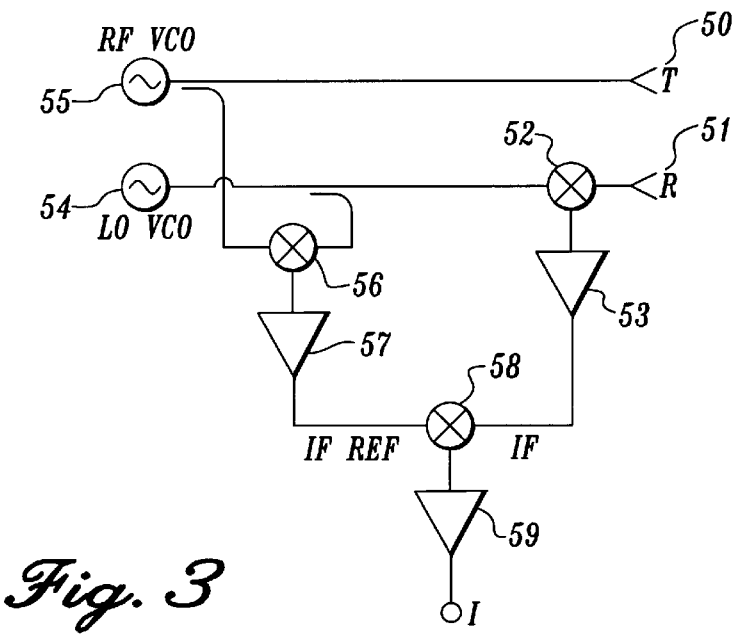
FIG. 3 is a schematic of a preferred bistatic, heterodyne, in-phase transceiver.
Figure 3A:
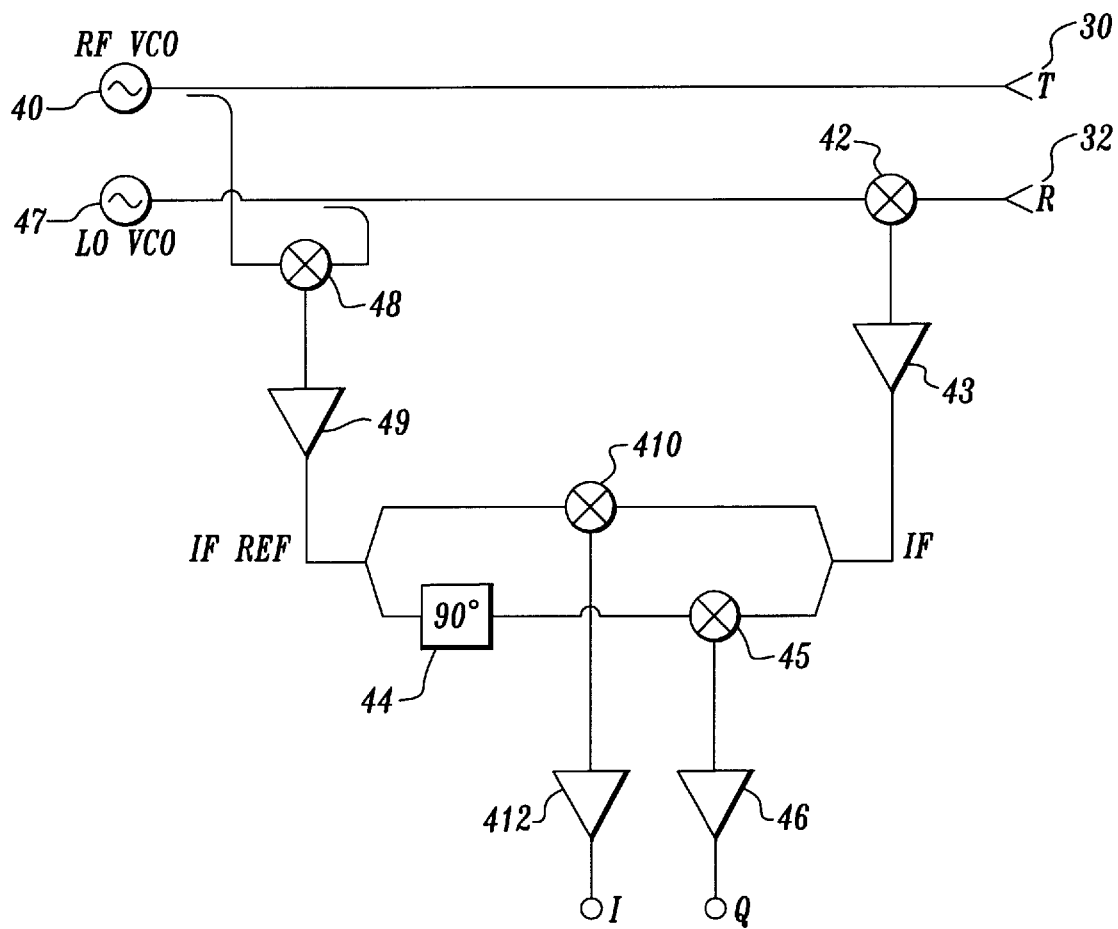
FIG. 3a is a schematic of a bistatic, heterodyne, quadrature receiver.

For the cylindrical system, a bi-static heterodyne, in-phase only transceiver (FIG. 3) is preferred. In this transceiver, the RF VCO wideband signal is transmitted directly by the transmit antenna 50. The received signal is received by the receiver 51 mixed in a mixer 52 and amplified (amplifier 53 to down-convert the received signal to the intermediate frequency (IF). The LO VCO oscillator 54 is offset in frequency from the RF VCO oscillator 55 by the IF frequency. To maintain coherence, an IF REF signal is obtained by mixing the RF VCO and LO VCO signals with a second mixer 56. This mixed signal is amplified and filtered in the amplifier 57 to remove higher frequency mixing products. Mixing the IF and IF REF signals in the final mixer 58 and amplifying in the final amplifier 59 yields the in-phase signal (I). Alternative transceivers may be used including but not limited to those in 08/440,279. More preferred is bi-static heterodyne in-phase and quadrature transceiver (FIG. 3a) because the in-phase only transceiver requires data from the entire scanned volume whereas using the in-phase and quadrature transceiver permits shifting the origin or reference position to the center of the scan thereby permitting digitizing of data in a reduced volume surrounding the target.

A-D CONVERTER

The wideband data is sampled vertically along the array and angularly over the 360° aperture and is digitized by an Analog to Digital converter (A/D) for subsequent storage in the computer.

COMPUTER AND DISPLAY

After digitizing, the reconstruction algorithm discussed below is applied to a segment of the 360° data to reconstruct a three-dimensional image of the target from a single viewing angle. The three-dimensional image is then collapsed into a fully-focused two-dimensional image of the target for display on the computer. A number of these viewing angles can then be integrated into a single computer animation showing a smooth rotation of the image of the target under surveillance.

OTHER COMPONENTS

The VCO DRIVERS board, ARRAY-CPU INTERFACE board, Analog to Digital converter (A/D) and other detailed components are set forth in 08/440,279 hereby further incorporated by reference.

DERIVATION OF IMAGE RECONSTRUCTION ALGORITHM

The image reconstruction algorithm derived in this section extends the work of Soumekh. Notation used is consistent with that used by Soumekh.

Figure 4:
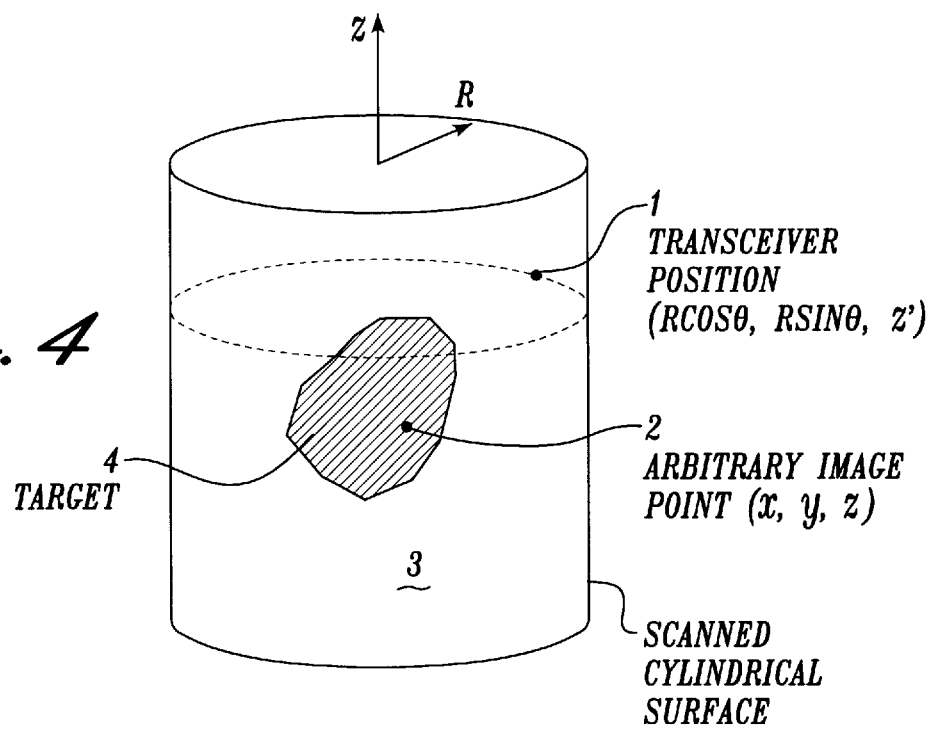
FIG. 4 is a coordinate definition diagram.

The measurement configuration is shown in FIG. 4, where the primed coordinates represent the transceiver position 1, and the unprimed coordinates represent a single target point 2 in the target or image space 3. If the target 3 is characterized by a reflectivity function, f(x,y,z), then the response measured at the transceiver position 1 will be the superposition of the reflectivity function times the round trip phase to the target 4. The round-trip phase is $$2k\sqrt{(R\cos\theta - x)^2 + (R\sin\theta - y)^2 + (z - z')^2} \quad (1)$$

The response measured at the transceiver position (1) is $$s(\theta, \omega, z) = \iiint f(x, y, z) e^{j2k\sqrt{(R\cos\theta-x)^2+(R\sin\theta-y)^2+(z-z')^2}} dx\,dy\,dz \quad (2)$$

where k=ω/c is the wavenumber, and the amplitude decay with range is not considered since it will have little impact on focusing the image. If needed, amplitude decay with range may be compensated for in the raw data by applying a numerical gain to the data from the transceiver. The numerical gain increases with range.

Alternatively, the data could be collected in the time domain, as is common with acoustic data. In this case, the data in Equation 2 will be obtained by Fourier Transforming the gathered data, which is the echoed data in the time domain.

The exponential term in Equation 2 represents a spherical wave which is decomposed into plane wave components, $$e^{j2k\sqrt{(R\cos\theta-x)^2+(R\sin\theta-y)^2+(z-z')^2}} = \quad (3)$$

$$\iint e^{j2k_r\cos\phi(R\cos\theta-x)+j2k_r\sin\phi(R\sin\theta-y)+jk_z(z-z')} d\phi\,dk_z$$

This decomposition indicates that the spherical wave can be decomposed into equal amplitude and phase plane wave components emanating from the target point at (x,y,z). The angle of each plane wave component in the x-y plane is φ which has limits of +/−π/2. For propagating plane waves, the limits of the z-component of the wavenumber will be $k_z$, ∈[−2k,2k]. The dispersion relation for the plane wave components is $$k_x^2+k_y^2+k_z^2=(2k)^2 \quad (4)$$

or defining $k_r$ to be the wavenumber component in the x-y plane $$k_r = \sqrt{k_x^2 + k_y^2} = \sqrt{4k^2 - k_z^2} \quad (5)$$

Using the plane-wave decomposition (5) in (2) the measured data can be expressed as $$s(\theta, \omega, z) = \quad (6)$$

$$\iint e^{j2k_rR\cos(\theta-\phi)}\{\iiint f(x, y, z) e^{-j2(k_r\cos\phi)x - j2(k_r\sin\phi)y - jk_zz}dx\,dy\,dz\} \cdot e^{jk_zz'}d\phi\,dk_z$$

The term inside the { } represents a three-dimensional Fourier Transform of the target reflectivity sampled on a non-uniform grid. Defining a three dimensional Fourier Transform pair as $$f(x,y,z) \Leftrightarrow F(2k_r \cos\phi, 2k_r \sin\phi, k_z) \quad (7)$$

Yields, $$s(\theta, \omega, z) = \iint e^{j2k_rR\cos(\theta-\phi)}F(2k_r\cos\phi, 2k_r\sin\phi, k_z)e^{jk_zz'}d\phi\,dk_z \quad (8)$$

The integral over $k_z$, is an inverse Fourier Transform, so taking the Fourier Transform with respect to z of both sides and dropping the distinction between z and z' yields $$s(\theta, \omega, k_z) = \int_{-\pi/2}^{\pi/2} e^{j2k_rR\cos(\theta-\phi)}F(2k_r\cos\phi, 2k_r\sin\phi, k_z)d\phi \quad (9)$$

Defining $$F_p(\phi,2k_r,k_z) \equiv F(2k_r \cos\phi, 2k_r \sin\phi, k_z) \quad (10)$$

$$g(\theta,k_r) \equiv e^{j2k_rR\cos\phi} \quad (11)$$

yields $$S(\theta, \omega, k_z) = \int_{-\pi/2}^{\pi/2} g(\theta - \phi, k_r) F_P(\phi, 2k_r, k_z) d\phi \quad (12)$$

which represents a convolution in the θ domain $$S(\theta,\omega,k_z) = g(\omega-\phi,k_r) * F_p(\phi,2k_r,k_z) \quad (13)$$

Taking the Fourier Transform with respect to θ and denoting the Fourier domain for θ by ξ, the convolution becomes a multiplication $$S(\xi,\omega,k_z) = \tilde{F}_p(\xi 2k_r,k_z) G(\xi,k_r) \quad (14)$$

or $$\tilde{F}_p(\xi, 2k_r, k_z) = \frac{S(\xi, \omega, k_z)}{G(\xi, k_r)} \quad (15)$$

Denoting Fourier Transformation or its inverse using a script $\mathfrak{I}$ yields $$F(2k_r\cos\theta, 2k_r\sin\theta, k_z) = \mathfrak{I}_{(\xi)}^{-1}\left[\frac{S(\xi, \omega, k_z)}{G(\xi, k_r)}\right] \quad (16)$$

The term in the denominator of (16) can be computed numerically by performing the Fourier Transform using the FFT on an angularly sampled version of (11), or it may be determined analytically for $\xi \ll 2k_r R$ using a definition of the Hankel function of the first kind ξ order and its asymptotic form $$G(\xi, 2k_r) = H_\xi(2k_r R) e^{j\pi\xi/2} \approx e^{-j\sqrt{4k_r^2 R^2 - \xi^2}} \quad (17)$$

This yields the simplest form of the inversion $$F(2k_r\cos\theta, 2k_r\sin\theta, k_z) = \mathfrak{I}_{(\xi)}^{-1}\left[S(\xi, \omega, k_z) e^{-j\sqrt{4k_r^2 R^2 - \xi^2}}\right] \quad (18)$$

where $2k_r\cos\theta = k_x$ and $2k_r\sin\theta = k_y$ in the spatial frequency domain. The data will be non-uniformly sampled in the spatial frequency domain and will therefore need to be interpolated onto a uniform $(k_x, k_y, k_z)$ grid prior to computation of the final three-dimensional inverse Fourier Transform that yields the reconstructed image in rectangular coordinates $$f(x, y, z) = \mathfrak{I}_{(k_x,k_y,k_z)}^{-1}\left[\mathfrak{I}_{(\xi)}^{-1}[S(\xi, \omega, k_z) e^{-j\sqrt{4k_r^2 R^2 - \xi^2}}]\right] \quad (19)$$

The discussion above shows how the gathered data can be inverted to obtain the target's reflectivity function or image. The steps that must be performed to reconstruct this image are summarized below.

Image Reconstruction Algorithm The steps required to implement the reconstruction technique on a computer are outlined below. The data is discretized in $(\phi,\omega,z)$ and the image is discretized in $(x,y,z)$. Fourier Transforms will typically be done using the discrete Fast Fourier Transform algorithm.

Reconstruction Algorithm

1. Gather sampled data, $s(\phi,\omega,z)$, from the transceiver over a cylindrical aperture. If the sampled data is available with only one or the other of the real component (I) or the imaginary component (Q), the remaining component may be derived from the sampled data using the Hibert Transform as discussed in D. Slater NEAR FIELD ANTENNA MEASUREMENTS, Artech House, Boston, Mass. 1991.

2. Perform 2-D FFT of this data with respect to φ and z to obtain $S(\xi,\omega,k_z)$.

3. Multiply by a phase-factor and perform 1-D inverse $$\mathfrak{I}_{(\xi)}^{-1}[S(\xi, \omega, k_z) e^{-j\sqrt{4k_r^2 R^2 - \xi^2}}] \quad (20)$$

4. Interpolate this data onto uniformly sampled $(k_x, k_y, k_z)$ grid from the uniformly sampled $(\phi,\omega,k_z)$ data.

$$F(k_x, k_y, k_z) = \quad (21)$$

$$\mathfrak{I}_{(\xi)}^{-1}[S(\xi, \omega, k_z) e^{-j\sqrt{4k_r^2 R^2 - \xi^2}}]|_{\theta=\tan^{-1}(k_y/k_x)}$$

$$\omega = \frac{c}{2}\sqrt{k_x^2+k_y^2+k_z^2}$$

$$k_r = \sqrt{k_x^2+k_y^2}$$

5. Perform the 3-D inverse FFT.

$$f(x,y,z) = \mathfrak{I}^{-1}(k_x,k_y,k_z)[F(k_x,k_y,k_z)] \quad (22)$$

6. Compute the magnitude of the image data.
7. Render/display the image(s).

Figure 5:
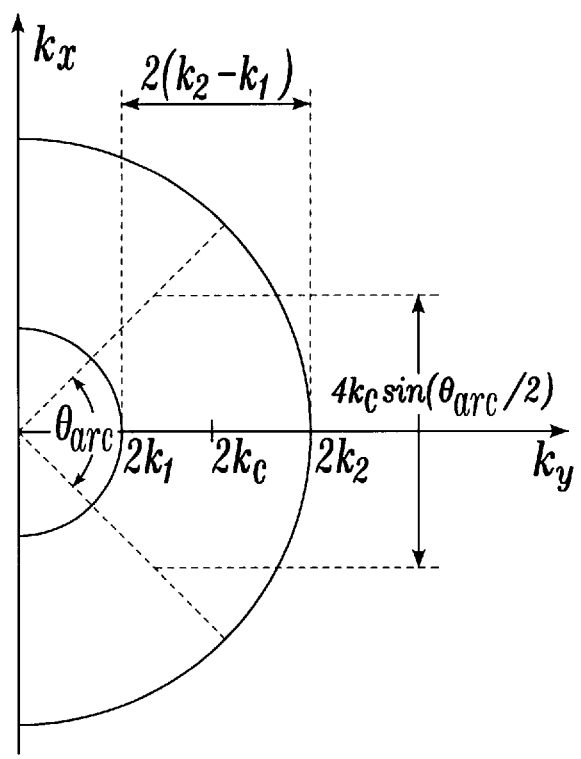
FIG. 5 is a diagram quantifying resolution.
Figure 6:
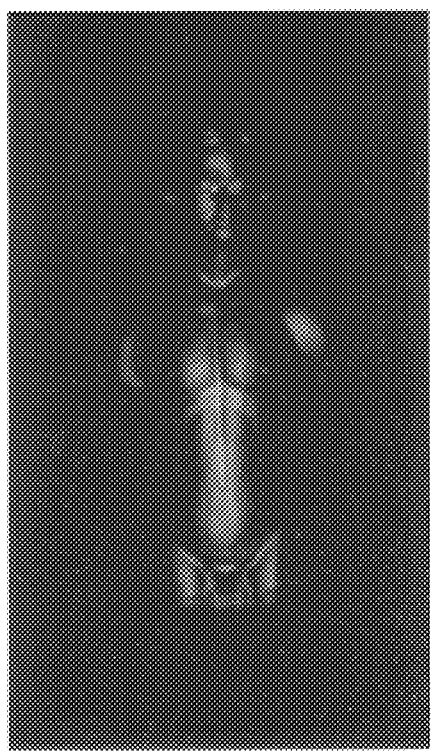
FIG. 6 is an obverse image of a mannequin made with a planar scan.
Figure 7:
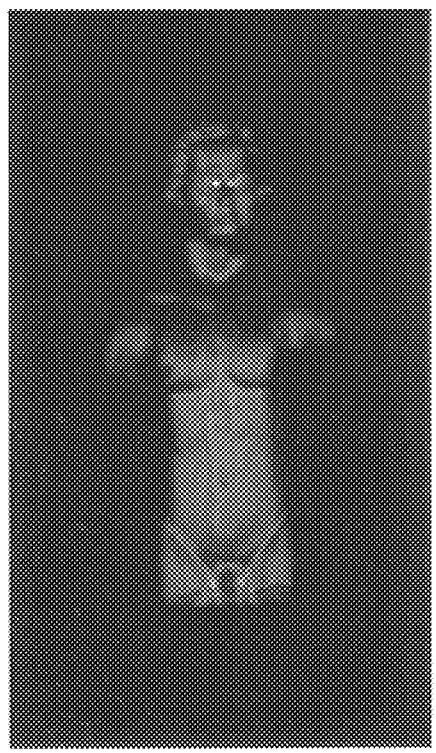
FIG. 7 is an obverse image of a mannequin made with a cylindrical scan.
Figure 8:
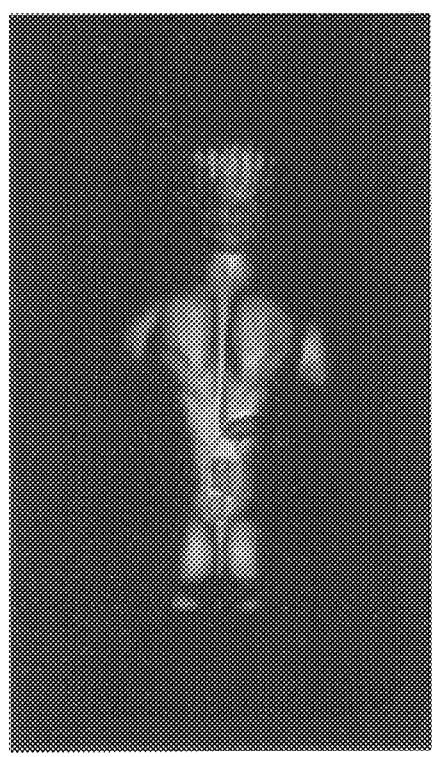
FIG. 8 is a reverse image of a mannequin made with a planar scan.
Figure 9:
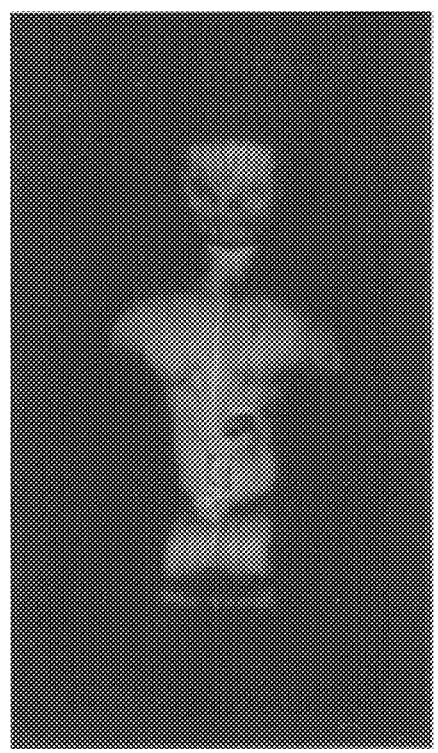
FIG. 9 is a reverse image of a mannequin made with a cylindrical scan.

This image reconstruction technique relies on formation of the image in the spatial frequency domain. The resolution obtained in the image can be determined by examining the extent or width of the coverage in the spatial frequency domain. For the cylindrical image reconstruction, the spatial frequency coverage is of a polar region shown in FIG. 5. Approximating the polar region as rectangular results in a horizontal cross range resolution of $$\delta_x = \frac{\lambda_c}{4\sin(\theta_{arc}/2)} \quad (23)$$

where $\lambda_c$ is the wavelength at the center frequency.

The vertical resolution will be determined by $\theta_b$, the lesser of the antenna full beamwidth or the angle subtended by the aperture in the z direction. The width of the spatial frequency coverage in the z direction is approximately $4k_c\sin(\theta_b/2)$. This results in a vertical cross-range resolution of $$\delta_z = \frac{\lambda_c}{4\sin(\theta_b/2)} \quad (24)$$

The spatial frequency width in the $k_y$ direction is $2(k_2 - k_1)$ where $k_1$ and $k_2$ are the wavenumbers at the low and high frequencies of the system. This width results in a range resolution of approximately $$\delta_y = \frac{2\pi}{2(k_2 - k_1)} = \frac{c}{2B} \quad (25)$$

where c is the speed of light and B is the temporal frequency bandwidth of the system.

COMPUTER INSTRUCTIONS

The steps of the reconstruction algorithm reside on the digital computer as (I) a first set of instructions for receiving data from the A/D converter, (ii) a second set of instructions for computing a two-dimensional Fourier transform of the received data for each frequency, (iii) a third set of instructions for multiplying the two-dimensional Fourier transform by a phase factor and computing a one-dimensional inverse Fourier transform, (iv) a fourth set of instructions for interpolating the one-dimensional inverse Fourier transform onto a uniformly sampled grid and forming an interpolated product, (v) a fifth set of instructions for computing a three-dimensional inverse transform of the interpolated product and obtaining a complex cylindrical three-dimensional image, (vi) a sixth set of instructions for computing a magnitude of the complex cylindrical three-dimensional image and obtaining a cylindrical three-dimensional image, and (vii) a seventh set of instructions for displaying the cylindrical three-dimensional image.

IMAGING

Reconstructing a large number of frames, 8–128, preferably 32–128 frames, permits smooth transitions between images, making the results suitable for computer animation at a rate from about 4 to 32 frames per second. It is further preferred that the frames are obtained from overlapping arc segments of data to improve smooth transitions. By observing a full animation, the subject is viewed from all angles without requiring inspector examination of separate still images.

The actual data processing of the above described seven steps produces a single image from a single viewing angle or arc segment of the 360° data. Overlapping arc segments permits viewing around corners, within depressions or other topographical perturbations of the target. For example, for imaging a clothed person, an imaging sequence may use 90° arc segments overlapped in 10° increments, or 0°–90°, 10–100°, . . . , 350°–80°, to form 36 images with illuminations centered at 10° increments. Each frame or arc segment reconstruction is computationally intensive. Therefore, high-speed image reconstruction is preferably achieved with high-speed parallel computer processors. To overcome difficulties of shared access to the data that is overlapped by a plurality of parallel computer processors, it is preferred that each arc segment reconstruction is accomplished by a single processor module. Each processor module receives its arc segment data from a digital multiplexer. Use of the multiplexer permits presenting data that is identical in an overlap to several of the processor modules simultaneously, permitting highly efficient video image reconstruction. Although efficient and fast because each processor module operates independently, more computer memory is needed for redundancy of data storage. Use of the multiplexer further permits near real time reconstruction of the image data. Reconstruction of the first arc segment may commence as soon as the first arc segment data are received. It is not necessary to wait until the scan has completed a full 360° rotation.

EXAMPLE 1

An experiment was performed to compare the image obtained with a planar aperture wideband holographic system to an image obtained with a cylindrical wideband holographic system according to the present invention.

The reconstruction algorithm was fully implemented on a Sun workstation in the C programming language. A first system utilized a single channel millimeter wave transceiver mounted on an x-y scanner in cooperation with a rotating platform. The rotary platform was used to rotate the subject to be imaged by small angular increments between vertical scans. Although convenient, for laboratory imaging, the x-y scanner in cooperation with the rotating platform required up to 20 minutes to collect 360° of data.

The imaging target was a mannequin torso having a concealed object. FIGS. 6–9 show the dramatic improvement in image quality that has been obtained by using a cylindrical aperture instead of a planar aperture. The images from both planar and cylindrical systems were taken at between 90 to 100 GHz frequencies. The planar aperture images FIGS. 6 and 8 exhibited more shadows because the planar aperture width of 40 cm and depth of 60 cm corresponds to only 37° of angular coverage whereas the cylindrical aperture exhibited fewer shadows using 120° of 360° data FIGS. 7 and 9.

EXAMPLE 2

An experiment was conducted to demonstrate the system with a person with a concealed object. In this example, a 128 element 27–33 GHz linear array was used in a vertical position in combination with a rotary platform. This system acquired 360° of data in less than several seconds, about 2.5 seconds.

Figure 10:
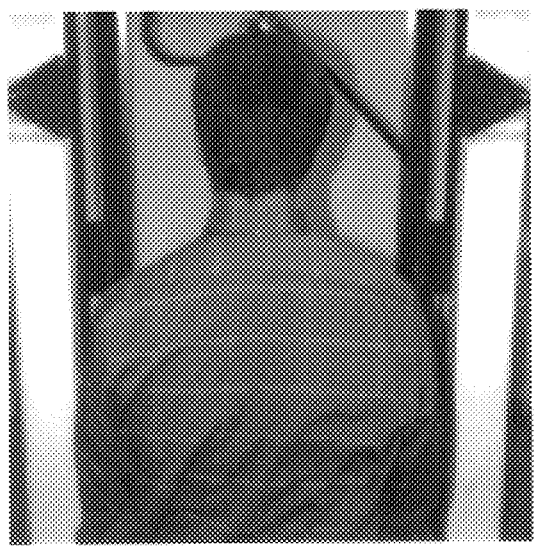
FIG. 10 is an obverse image of a person made with an optical camera.
Figure 11:
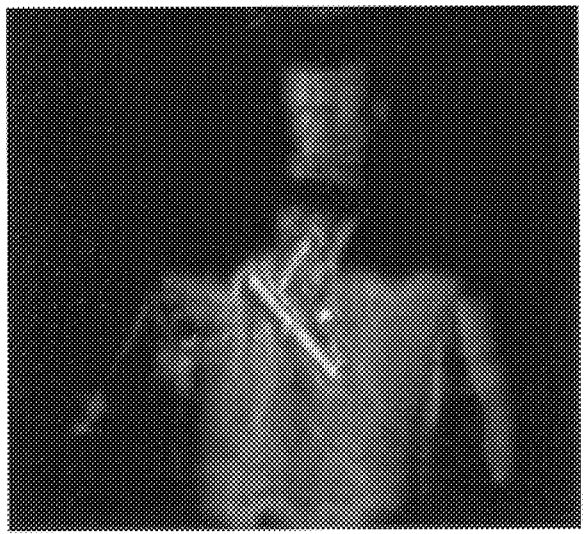
FIG. 11 is an obverse image of a person made with a cylindrical scan.

FIG. 10 shows a photograph of a man with a concealed object and FIG. 11 shows the cylindrical image revealing the object, a Glock-17 handgun.

EXAMPLE 3

Figure 12:
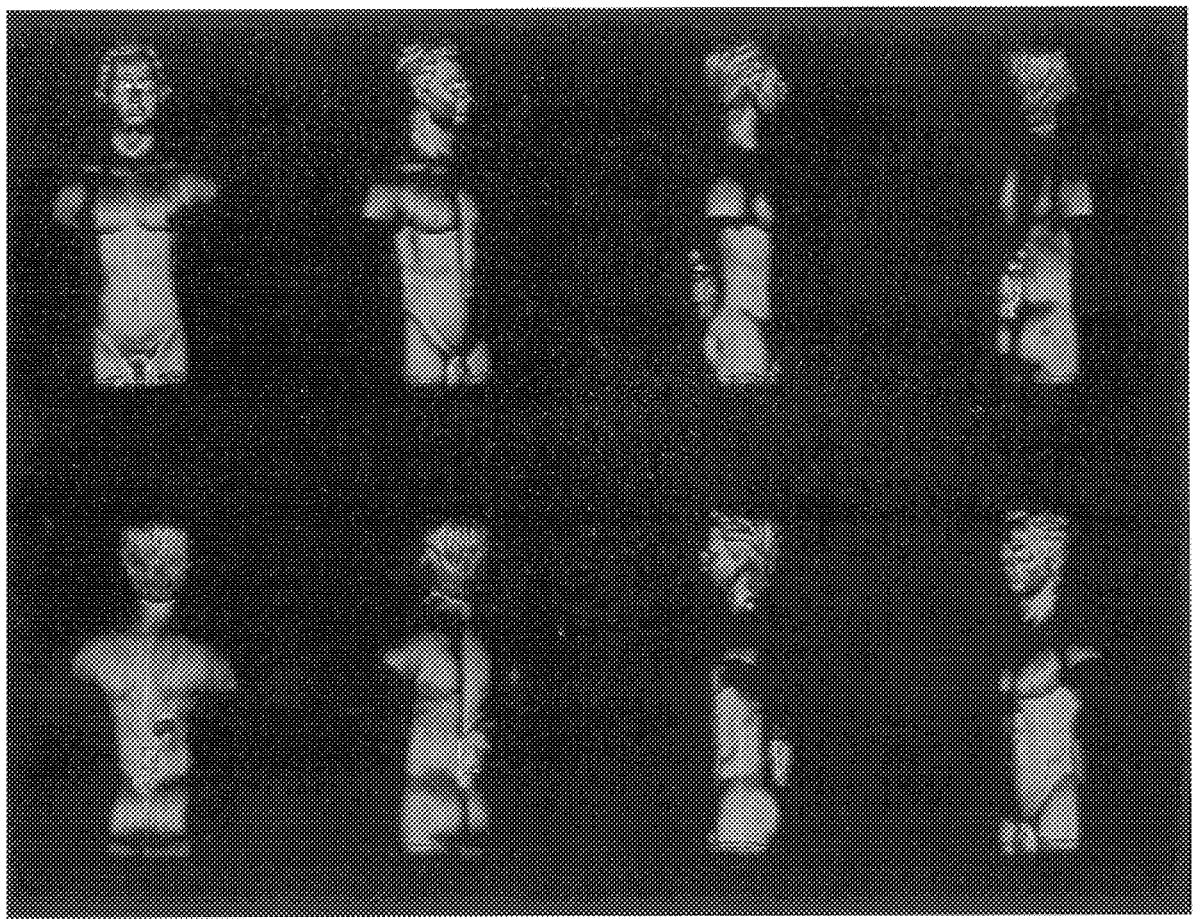
FIG. 12 is a series of images illustrating the computer animation.

An experiment was conducted to demonstrate reconstruction of sequential overlapping data. FIG. 12 shows a mannequin with a small handgun taped to its back and covered with a cotton T-shirt, imaged over a 360° aperture. Eight of 64 view angles are shown in FIG. 12. Computer animation of the 64 view angles resulted in smooth animation of the images at frame rates of 4–32 frames per second. By observing the full animation, the target is viewed from all angles without requiring separate examination of a plurality of still images. The animation further preserves the three-dimensional nature of the target with concealed objects appearing "off" the target in several frames of the animation.

CLOSURE

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

We claim:

1. A holographic apparatus for near real-time imaging of a target, said apparatus utilizing millimeter wave radiation having a plurality of frequencies from about 1 to about 110 GHz, comprising:

(a) a holographic array having a plurality of antenna units spaced apart from about 0.25 to about 3 wavelength, wherein each unit sends and/or receives millimeter wave radiation, said array spaced apart from said target;

(b) a holographic wideband transceiver for operating said antenna units and providing each unit with millimeter wave radiation source, then receiving high frequency millimeter wave radiation reflection from said target and collected by the unit, then making an output;

(c) an analog to digital converter for converting said output to a corresponding digital signal; and (d) a computer for applying a three dimensional reconstruction algorithm to the corresponding digital signal that preserves an unlimited depth of field, wherein the improvement comprises:

said computer is a digital computer having,
 (I) a first set of instructions for receiving data from the A/D converter,
 (ii) a second set of instructions for computing a two-dimensional Fourier transform of the received data for each frequency,
 (iii) a third set of instructions for multiplying the two-dimensional Fourier transform by a phase factor and computing a one-dimensional inverse Fourier transform,
 (iv) a fourth set of instructions for interpolating the one-dimensional inverse Fourier transform onto a uniformly sampled grid and forming an interpolated product,
 (v) a fifth set of instructions for computing a three-dimensional inverse transform of the interpolated product and obtaining a complex cylindrical three-dimensional image,
 (vi) a sixth set of instructions for computing a magnitude of the complex cylindrical three-dimensional image and obtaining a cylindrical three-dimensional image, and
 (vii) a seventh set of instructions for displaying the cylindrical three-dimensional image.

2. The apparatus as recited in claim 1, wherein said antenna units are bistatic.

3. The apparatus as recited in claim 1, wherein said output is an in-phase output.

4. The apparatus as recited in claim 1, wherein the first set of instructions further comprises:

a subset of instructions for deriving complex data (Q) from in-phase data (I).

5. The apparatus as recited in claim 1, said array comprises:

a linear array, moved by a mechanical means during transmission and receipt of said high frequency millimeter wave radiation, thereby providing a simultaneous scan of source and reflection millimeter wave radiation.

6. The apparatus as recited in claim 1, wherein said transceiver is a bistatic, heterodyne, in-phase output transceiver.

7. A method of holographic surveillance of a target, comprising the steps of:

(a) scanning a cylindrical aperture with a holographic array having a plurality of antenna units spaced apart from about 0.25 to about 3 wavelength, wherein each unit sends and/or receives millimeter wave radiation, said array spaced apart from said target;

(b) operating individual antenna elements with a wideband holographic transceiver system and providing each unit with a wideband millimeter wave radiation source, then receiving wideband millimeter wave radiation reflection from said target and collected by the unit(s), then making an output;

(c) converting said output in an A/D converter to a corresponding digital signal; and (d) applying a three dimensional reconstruction algorithm to the digital signal that preserves a low f-number by the steps of:
 (I) receiving data from the A/D converter,
 (ii) computing a two-dimensional Fourier transform of the received data for each frequency,
 (iii) multiplying the two-dimensional Fourier transform by a phase factor and performing a one-dimensional inverse Fourier transform and forming an inversion,
 (iv) interpolating the inversion onto a uniformly sampled grid and forming an interpolated product,
 (v) computing a three-dimensional inverse transform of the interpolated product and obtaining a complex three-dimensional image,
 (vi) computing a magnitude of the complex three-dimensional image and obtaining a cylindrical three-dimensional image, and
 (vii) displaying the three-dimensional image.

8. The method as recited in claim 7, wherein applying the three dimensional reconstruction algorithm includes applying a transform to derive an imaginary digital signal to reconstruct a holographic image.

9. The method as recited in claim 7, wherein receiving the data further comprises:

deriving complex data (Q) from in-phase data (I).

* * * * *

UNITED STATES PATENT AND TRADEMARK OFFICE
CERTIFICATE OF CORRECTION

PATENT NO.   : 5,859,609
DATED        : January 12, 1999
INVENTOR(S)  : Sheen et al.

It is certified that error appears in the above-identified patent and that said Letters Patent is hereby corrected as shown below:

Column 6,
Formula (2), please replace "$\iiint f(x,y,z)e^{j2k\sqrt{R\cos\Theta-x)2+(R\sin\Theta-y)2+(z-z')2}}$" with
-- $\iiint f(x,y,z)e^{j2k\sqrt{R\cos\Theta-x)^2+(R\sin\Theta-y)^2+(z-z')^2}}$ --.
Formula (3), please replace "$e^{j2k\sqrt{R\cos\Theta-x)2+(R\sin\Theta-y)2+(z-z')2}}$" with
-- $e^{j2k\sqrt{R\cos\Theta-x)^2+(R\sin\Theta-y)^2+(z-z')^2}}$ --.
Formula (5), please replace "$\sqrt{4k^2-kz'2}$" with -- $\sqrt{4k^2-kz'^2}$ --.

Column 7,
Formula (13), please replace "$=g(\omega-\Phi,k_r)*F_p(\Phi,2k_r,k_z)$" with
-- $=g(\Theta-\Phi,k_r)*F_p(\Phi,2k_r,k_z)$ --.
Formula (14), please replace "$=Fp(\xi 2kr,kz)G(\xi,kr)$" with -- $=Fp(\xi,2kr,kz)G(\xi,kr)$ --.
Line 64, please replace "$(\Phi,\omega,z)$" with -- $(\Theta,\omega,z)$ --.

Column 8,
Line 2, please replace "$s(\Phi,\omega,z)$" with -- $s(\Theta,\omega,z)$ --.
Line 9, please replace "...respect to $\Phi$ and z..." with -- respect to $\Theta$ and z --.
Line 11, please add the words -- FFT to obtain -- after the word "inverse".
Line 17, please replace "$(\Phi,\omega,k_z)$" with -- $(\Theta,\omega,k_z)$ --.
Formula (22), please replace "$(k_x,k_y,k_z)[F(k_x,k_y,kz)$" with -- $(k_x,k_y,k_z)[F(k_x,k_y,kz)$ --.

Signed and Sealed this

Twenty fifth Day of September, 2001

Attest:

NICHOLAS P. GODICI

*Attesting Officer*   *Acting Director of the United States Patent and Trademark Office*